United States Patent
Daniel (10) Patent No.: US 9,560,426 B1
(45) Date of Patent: Jan. 31, 2017

(54) SYSTEM AND METHOD FOR GROUP TRACKING AND DISPLAYING A PLURALITY OF WIRELESS TRACKING DEVICES ON ROTATIONAL MAPS ORIENTED BY ONE OR MORE INDIVIDUALS BEING TRACKED

(76) Inventor: Isaac S. Daniel, Miramar, FL (US)

( * ) Notice: Subject to any disclaimer, the term of this patent is extended or adjusted under 35 U.S.C. 154(b) by 55 days.

(21) Appl. No.: 13/460,444

(22) Filed: Apr. 30, 2012

Related U.S. Application Data (63) Continuation-in-part of application No. 12/315,547, filed on Dec. 4, 2008.

(60) Provisional application No. 61/480,230, filed on Apr. 28, 2011.

(51) Int. Cl.
- *H04Q 5/22* (2006.01)
- *G01S 1/00* (2006.01)
- *H04W 24/00* (2009.01)

(52) U.S. Cl.
CPC ........................................ *H04Q 5/22* (2013.01)

(58) Field of Classification Search
CPC ........................................................ H04Q 5/22
USPC ....................................................... 340/10.3
See application file for complete search history.

(56) References Cited

U.S. PATENT DOCUMENTS

| | | | | |
|---|---|---|---|---|
| 6,278,370 B1* | 8/2001 | Underwood | ....... | G08B 21/0216 340/539.1 |
| 6,975,873 B1* | 12/2005 | Banks | ................... | H04W 64/00 455/456.1 |
| 7,265,666 B2* | 9/2007 | Daniel | ..................... | A43B 3/00 340/539.1 |
| 8,032,155 B2* | 10/2011 | Klassen | ............... | G01C 21/367 340/995.14 |
| 2002/0055978 A1* | 5/2002 | Joon-Bo | ............... | H04W 84/20 709/209 |
| 2007/0229350 A1* | 10/2007 | Scalisi | .................... | G06F 21/35 342/350 |

* cited by examiner

*Primary Examiner* — Jennifer Mehmood
*Assistant Examiner* — John Mortell
(74) *Attorney, Agent, or Firm* — Carol N. Green Kaul, Esq.

(57) ABSTRACT

A system and method for tracking a group of individuals comprising: a wireless tracking device provided to at least one or more individuals within a group, wherein the wireless tracking device is configured for bi-directional communications with a monitoring center that establishes dynamic geo-fencing limitations in real-time for all group members provided with the wireless tracking device based on the group's center of gravity as they travel, whereby the geofence is in constant motion, and the wireless tracking device is adapted to determine and store absolute location information of each wireless tracking device provided to group members; and viewing device configured for displaying identification information concerning each individual wireless tracking device within the group on a rotating map display oriented relative to the group leader's location information.

20 Claims, 8 Drawing Sheets

SYSTEM AND METHOD FOR GROUP TRACKING AND DISPLAYING A PLURALITY OF WIRELESS TRACKING DEVICES ON ROTATIONAL MAPS ORIENTED BY ONE OR MORE INDIVIDUALS BEING TRACKED

PRIORITY CLAIM

This patent application is a non-provisional continuation in part of, and claims priority to: U.S. Provisional Patent Application Ser. No. 61/480,230 titled "A System And Method For Group Tracking And Displaying A Plurality Of Wireless Tracking Devices On Rotational Maps Oriented By One Or More Individuals Being Tracked" filed Apr. 28, 2011; U.S. Non-Provisional patent application Ser. No. 12/315,547 titled "A System And Method For Group Tracking" filed Dec. 4, 2008. The entire disclosures of the afore-mentioned patent applications are incorporated by reference as if fully stated herein.

FIELD OF THE INVENTION

The present invention relates generally to a system and method for group tracking using an advanced communication system network for tracking and monitoring each individual in a group wherein each individual is provided with a wireless tracking device that can be selectively engaged by the individual to transmit an encoded signal containing the individual and/or the group's specific location to a monitoring center. Each member in the group's location is displayed on a map oriented by the group leader's location.

DESCRIPTION OF THE PRIOR ART

Mountain climbers, hikers, guided tours, boy scouts and military troops often travel outdoors to remote locations navigating unpredictable, difficult terrain in primitive surroundings with relatively little distance between each group member. Generally, the communications are organized with a centralized control, where the majority of the communications take place between the group leader and individual group members. External communications are similarly directed to, and through the group leader where only occasionally individual group members communicate directly with each other and/or the external world.

Emergencies often alter those communications dynamics as individual group members may need to transmit or receive external communications. Thus, it is no surprise that rescue parties often lose precious time locating individuals and/or the group because generally there is no readily implementable system and method for dynamically tracking the group and/or its individual members as they travel over remote terrain. In those circumstances, use of public wireless networks is often impossible or impractical because of nonexistent electrical or wireless service or there is limited access to necessary resources, e.g. power supply, to effectuate the communication. Satellite phones offer a limited solution as the cost of satellite service prohibits widespread general use. Thus, it would be useful to be able to track a group's movements both collectively and individually as they travel in remote locations to determine for example, their location at any given point in time. It would also be useful for the group to be able to provide information to the external world as to the group's and/or its individual member's geographical location at any given time.

The prior art suggests that Global Positioning Systems ("GPS") may offer a limited solution as it is widely used for other like applications, for e.g. (i) personal tracking systems where it records and reports individual's geographical position and/or the distance travelled from a fixed location; (ii) vehicle and personal navigational systems by providing maps and directions from a current location to the destination as well as reporting geographical position and other pertinent information, e.g. average speed travelled over the distance; (iii) geo-fencing by controlling the movement of an individual or a valuable asset from straying or being removed beyond a predefined area; and (iv) asset management systems which provide current geographical position of valuable movable assets.

The afore-mentioned groups usually travel from a common starting point to a common destination. Therefore, effective tracking of these groups will require elements of navigation assistance, particularly for the group leader, as well as elements of geo-fencing where the "fence" may be determined as the maximum allowable distance away from the group leader or the majority of the group members ("center of gravity"). However, unlike typical geo-fencing systems of the prior art, here the "fence" is dynamic as in constant motion. Likewise, applying strict asset management systems technology of the prior art would be ineffective as here, group tracking transactions are bi-directional and could be initiated either by group members and/or by the group leader. Thus, there exists a need to be able to track the location of a group collectively and/or individually where both the group leader and/or its members are in constant motion and are constantly changing directions. Similarly, there exists a need to facilitate bi-directional communications for mobile individuals traveling in a group in remote locations.

This invention satisfies these long felt needs in a new and novel manner and solves the foregoing problems that the prior art has been unable to resolve.

SUMMARY OF THE PRESENT INVENTION

The present invention relates generally to a system and method for group tracking wherein each individual within a group that is being monitored is provided with a wireless tracking device for bi-directional communications with a monitoring center, adapted to provide control modules which includes means for determining and storing the absolute location of said individual, and at least one other individual within the group's location information. Each individual's wireless tracking device has a unique identifier for identifying said individual with a monitoring center at a remote location.

The wireless tracking device is also provided with receiving means for receiving an activation signal from a monitoring center and/or the transmitting means of another article of footwear being worn by the group leader. An individual's wireless tracking device utilizes its determining means to determine whether it has direct access to a satellite network system. If it does, upon activation the individual's location information may be transmitted to a monitoring center at a remote location via the satellite network system. The satellite network system may include one of the following: a geosynchronous or low earth orbit satellite.

However, it is not uncommon for an individual's wireless tracking device within the group to lack direct access to the satellite network system. As such, the system and method of the invention provides means for dynamically creating a relay path of transmission to the satellite network system by querying nearby wireless tracking devices within the group being monitored until at least one wireless tracking device with direct access to the satellite network system is determined. Once that relay path of transmission is dynamically created, the communication means, which includes both transmitting and receiving means, for each wireless tracking device transmits an encrypted signal containing the individual's location information along that relay path to a monitoring center at a remote location via the satellite network system. The location information being transmitted to the monitoring center may include any one or more of the following: zero, one or more absolute geographical reference points for one, some or all individuals in the group that are being monitored. Accordingly, each individual group member's location information may be transmitted and stored for transmission to the monitoring center even though an individual's wireless tracking device may lack direct access to a satellite network system.

The transmitting means and the receiving means may comprise of a combined wireless transceiver with integrated radio and shared antennae, e.g. WiHLoN™, Zigbee, Bluetooth®, 802.11 series, or any other short range wireless protocol that is well known and used in the arts. Preferably, the transmitting means, receiving means and the encrypting means include a combined wireless transceiver like a Zigbee transceiver with an integrated radio and shared antennae.

The system and method employs IEEE 802.15.4 standard which is an open wireless technology standard for exchanging data from a coordinator to an end device, wherein a coordinator is a device which creates a network to be used. The end devices may join the network, based on network parameters, and establish communication. It operates in the globally 900 MHz radio frequency band and is aimed at transmitting and receiving low-bandwidth data to a network of devices while providing efficient battery consumption. This standard is generally used in homes and industrial settings for wireless monitoring. Global Positioning System (GPS) is a satellite based system which allows a GPS receiver to calculate its position (longitude, latitude and elevation) anywhere on earth. In a military setting, the system and method is the means of locating friendly military commanders and forces and also functions as an asset tracker. After troops are dismounted, the locations of the soldiers are unknown unless the leader has a line of sight which is a disadvantage to the squad leader. The wireless tracking device will allow each soldier to have location information be transmitted to the squad leader and the display device will illustrate their location and status on a rotating map display that is oriented according to the geographical coordinates of the squad leader. The display of the various locations of the individual group members may be oriented and/or rotated based on the coordinates of the group leader and in some embodiments other individual members of the group. This gives the squad leader the opportunity to locate soldiers beyond his/her line of sight and directional advantage if there is a necessity for the squad leader to provide directions or there is a search and/or rescue mission.

A primary object of the present invention is to provide a system and method for group tracking that overcomes the limitations of the prior art.

Another object of the present invention is to provide location information for individuals within a group as they travel over remote locations.

Still another object of the present invention is to provide a system and method wherein the monitoring center is able to identify and monitor the movements and/or activities of a group and or its individual members.

Another objective of the invention is to readily identify the identity and location of an individual within a group that is being monitored based on the rotating map display.

Yet another objective of the invention is to provide rotating maps that will rotate and orient themselves based on the group leader's geographical coordinates and as such the group leader can provide directions to an individual group member based on the group leader's perspective.

Still yet another objective of the invention is to provide rotating maps that will rotate and orient themselves based on a secondary leader's geographical coordinates and as such the secondary group leader can provide directions to other individual group members based on the secondary group leader's perspective.

Another objective of the invention is to provide a system and method for monitoring all individuals in a group in an expedient and efficient manner.

For a further and more fully detailed understanding of the present invention, various objects and advantages thereof, reference is made to the following detailed description and the accompanying drawings.

The foregoing and other objects and advantages will appear from the description to follow. In the description, references are made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

Further objectives and advantages of the present invention may be derived by referring to the detailed description and claims when considered in connection with the Figures, wherein like reference numbers refer to similar items throughout the Figures.

DETAILED DESCRIPTION OF THE PREFERRED EMBODIMENT

The following discussion describes in detail one embodiment of the system of the invention (and several variations of that embodiment). However, this discussion should not be construed as limiting the invention to those particular embodiments as practitioners skilled in the art will recognize numerous other embodiments as well. For definition of the complete scope of the invention, the reader is directed to appended claims.

Turning now descriptively to the drawings, in which similar reference characters denote similar elements throughout the several views.

Figure 1:
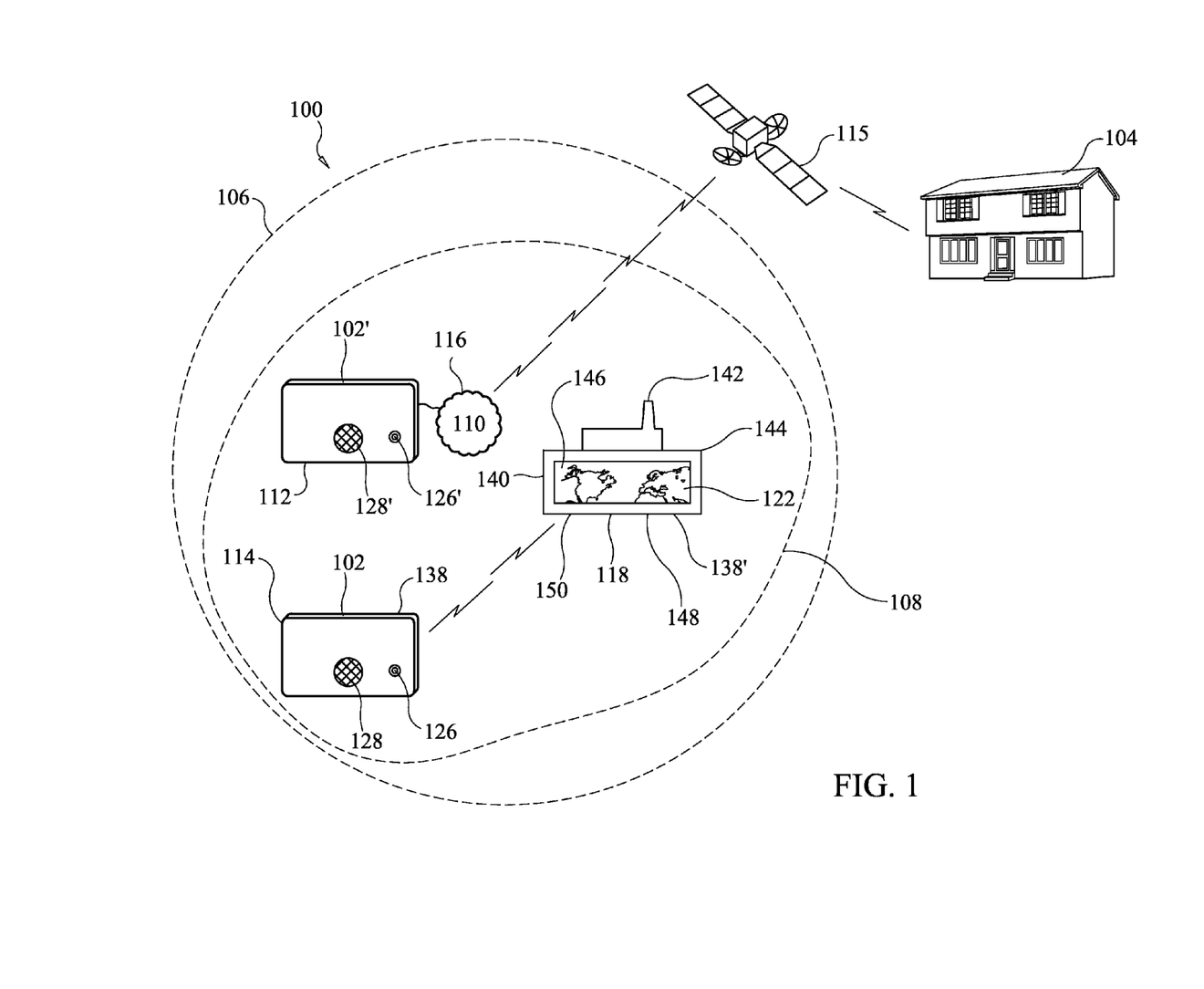
FIG. 1 is an illustrative view of the system of the present invention.
Figure 2A:
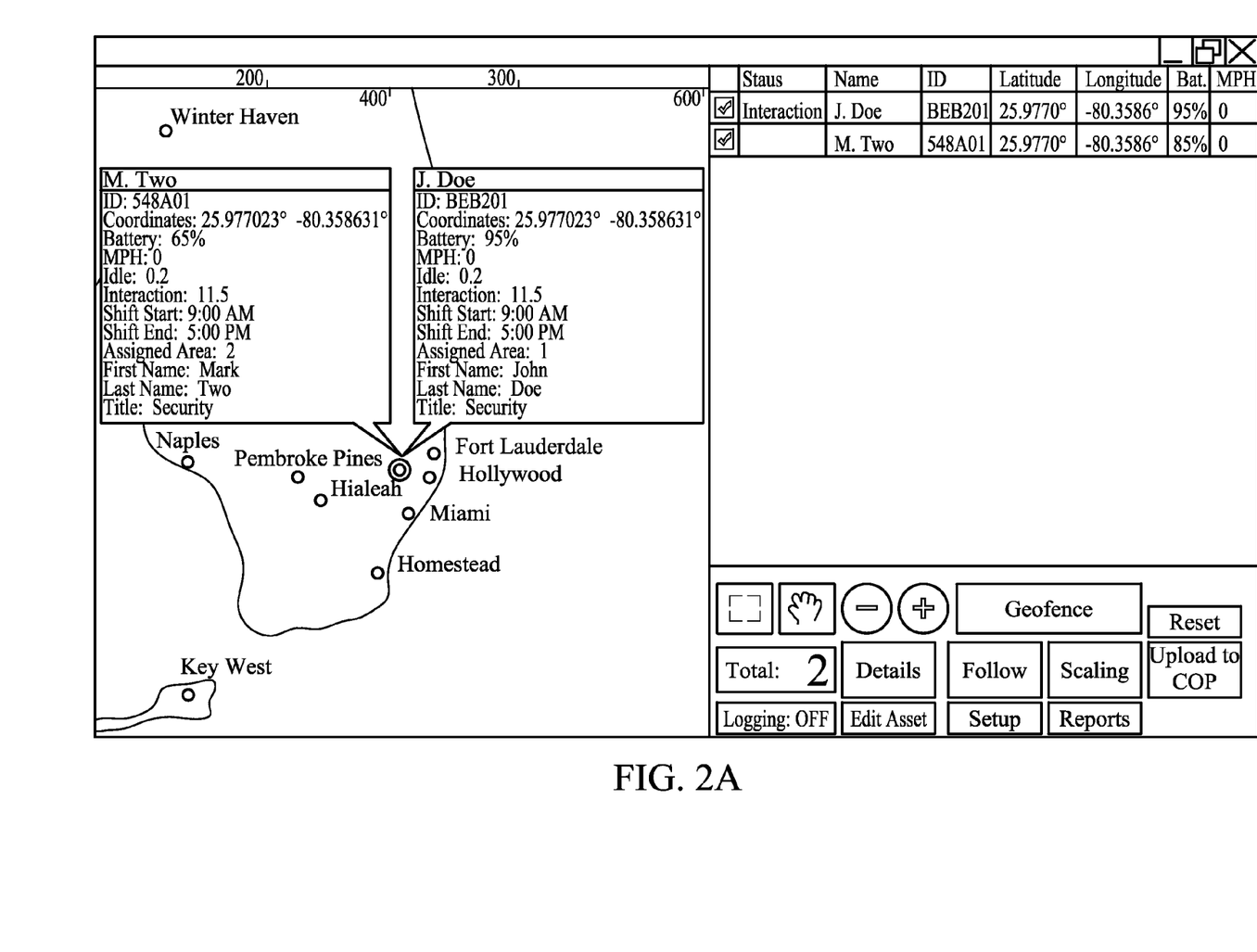
FIGS. 2A-2D are illustrative views of a system tracking different individuals according to an embodiment of the present invention.
Figure 2B:
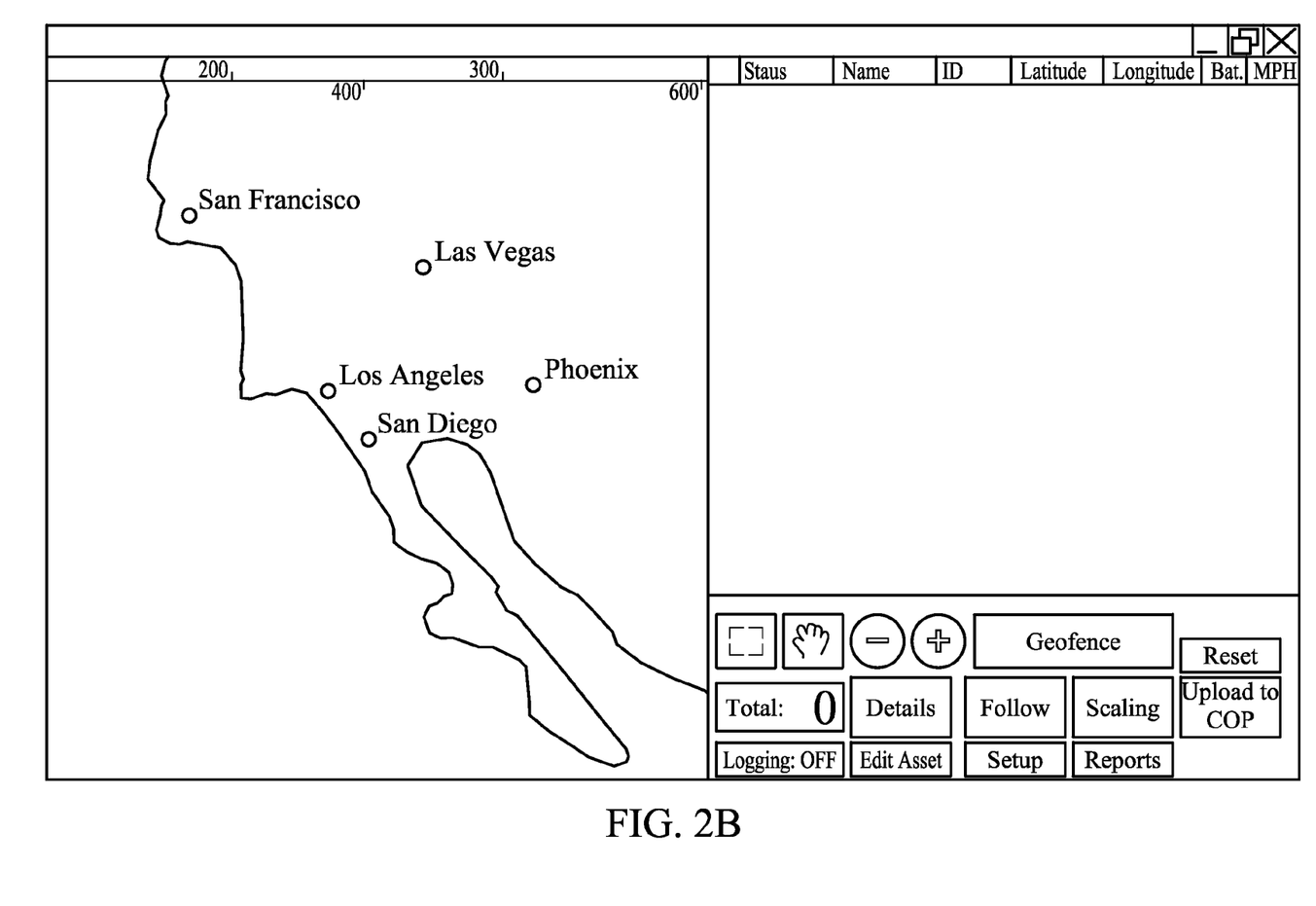
Figure 2C:
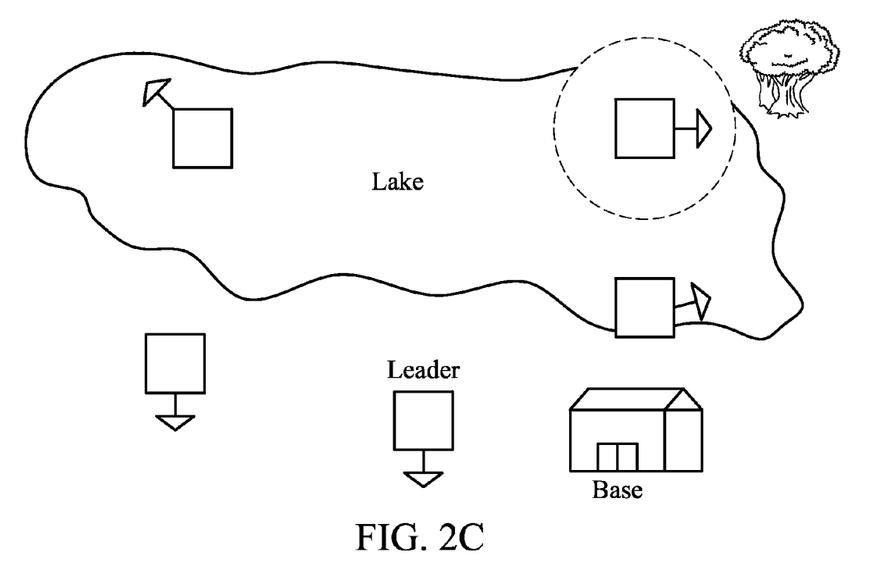
Figure 2D:
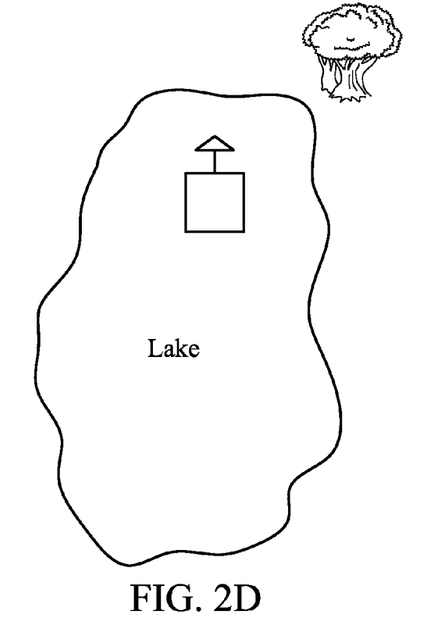

FIG. 1 is an illustrative view of the system 100 in accordance with an embodiment of the present invention. System 100 includes a wireless tracking device 102 provided to at least one or more individuals within a group. In some embodiments, the wireless tracking device 102 comprises of a lightweight, water resistant, battery powered device that may be embedded in an article of clothing, e.g. footwear, a vest or an armband.

The wireless tracking device 102 is configured for bi-directional communications with a monitoring center 104 that establishes dynamic geo-fencing limitations in real-time for all group members provided with the wireless tracking device 102 based on the group's center of gravity as they travel, whereby the geo-fence 106 is in constant motion with a dynamic perimeter 108, and the wireless tracking device 102 is adapted to determine and store absolute location information 110 of each wireless tracking device 102 provided to group members as well as their location information 110 relative to a group leader's location information 110'; communication means 112 for receiving an activation signal from a communications means 112 of another wireless tracking device 102' within the group and determining means 114 for determining said wireless tracking device's 102 direct access to a satellite network system 115; said communication means 112 for dynamically creating a relay path of transmission to a satellite network system 115 by querying nearby wireless tracking devices 102', 102", 102''' within the group until at least one wireless tracking device 102' with direct access to the satellite network system 115 is determined; communication means 112 for transmitting an encrypted signal 116 containing location information 110 of at least one individual within said group along a dynamically created relay path of transmission, where said individual's location information 110 is received and stored for transmission along the dynamically created relay path via said satellite network system 115; and viewing device 118 configured for displaying identification information 120 concerning each individual wireless tracking device 102 within the group on a rotating map display 122 oriented relative to the group leader's location information 110'.

Monitoring center 104 may be remote or local, and sets geo-fencing limitations for the group's members being monitored by their wireless tracking devices 102, 102', 102" in real-time based on the group's center of gravity as they travel. The geo-fence 106 may be defined as the maximum allowed distance between the group leader and for instance the majority of the group members ("center of gravity"), where the geo-fence 106 is in constant motion with a dynamic perimeter 108. This allows the monitoring center 104 to monitor the group as a whole and/or individual group members to determine whether geo-fencing limitations have been violated by a group member as it monitors each individual's wireless location as represented by his/her wireless tracking device 102 relative to the predefined geo-fencing limitations, i.e. relative distance between individual group members to confirm that individuals are still within predefined geo-fencing limitations. If during a tracking session, no geo-fencing limitations have been violated, monitoring center 104 will continue to monitor the individuals until the tracking session terminates by virtue of a predetermined condition, e.g. notification of group arriving at their target destination, pre-defined time has elapsed in combination with no alarm conditions being reported or determined, and/or any other suitable predetermined conditions for terminating the tracking session without compromising the safety of the tracked group.

If monitoring center 104 determines that an individual has strayed beyond the pre-defined geo-fencing limitations for the group, an alarm will be triggered at the monitoring center 104, wherein the monitoring personnel may require confirmation with the group leader, that the individual's location is known or that it is a false alarm as the group leader may not be aware of the missing individual. Accordingly, monitoring center 104 or the wireless tracking device 102 may transmit a message via SMS text through a GSM communications network 124 (not shown), and/or an encrypted alarm signal 116 over the satellite network system 115 notifying the group leader of the potentially alarming condition, i.e. missing individual.

Wireless tracking device 102 includes communication means 112 either electrically or mechanically connected to a computer microcontroller positioned within, for the receipt and transmissions of wireless communications through a wireless communications network: system 114 (not shown), which is preferably a satellite network system 115. Communication means 112 may include but is not limited to, a radio frequency transceiver, a radio frequency receiver, and/or a radio frequency transmitter. In embodiments where the wireless communication means 112 is a radio frequency receiver, the radio frequency receiver may be any type of radio frequency receiver, including, but not limited to, a positioning system receiver, such as a Global Positioning System ("GPS") receiver and a local positioning system receiver, such as a Wi-Fi positioning system receiver. In other embodiments, the communication means 112 may employ wireless protocols like Blue Tooth, ZigBee, 702.11 series, or a wireless modem, such as, but not limited to, a global system for mobile communications (GSM) modem, or any other short range wireless protocol that is well known and used in the arts and other future short range wireless protocol suitable for transmitting and receiving data. Communication means 112 are operative to transmit or receive electronic communications, i.e. data, text, sound, pictures, and the like via a short range wireless protocol, such as, but not limited to, a radio frequency receiver, a radio frequency transmitter, or a radio frequency transceiver. Preferably, communication means 112 comprises of a combined wireless transceiver with integrated radio and shared antennae, e.g. WiHLoWM, ZigBee, Bluetooth®, 802.11 series, or any other short range wireless protocol that is well known and used in the art, in mating engagement with an autonomous power supply, e.g. a rechargeable battery.

The communication means 112 may transmit at least one encrypted signal 116 containing the individual's wireless tracking device's location information 110 to a monitoring center 104, and/or a neighboring wireless tracking device 102'. The location information 110 may comprise of but is not limited to: an individual's absolute geographical location (latitude, longitude, or altitude), the date (the location information 110) was determined, time (the location information 110 was determined), the individual's geographical location relative to other group members within the tracked group and/or the individual's geographical location relative to the group leader's and/or the secondary group leader's wireless tracking devices 110', 110".

Wireless tracking device 102 includes an activation button 126, which may be selectively depressed to either activate and/or deactivate transmission of the individual's location information 110 to monitoring center 104. The activation button 126 may be covered by a switch cover 130 (not shown) that is hingedly connected to the exterior side of the wireless tracking device 102 by a hinge 132 (not shown). Preferably, the switch cover 130 (not shown) is semi-rigid in order to prevent accidental activation. In some embodiments as shown in FIG. 1, the activation button 126 is not secured by a switch cover 130 (not shown) but rather having been secured and waterproofed under the wireless device's exterior no additional switch cover 130 (not shown) is needed.

Wireless tracking device 102 also includes an alarm button 128, which may be electrically connected to a speaker 134 (not shown) capable of sounding an audio alarm; a single tone alert system 136 (not shown) sounding an alarm like Sonalert; or a microcontroller 138 electrically connected to the alarm button 128 programmed to flash a light thereon on receipt of an encrypted alarm signal 116 from monitoring center 104 as the monitoring center 104 may also transmit an alarm to the individual's wireless tracking device 102. In some embodiments, the alarm button 128 is configured to trigger a silent alarm that will be heard remotely at the local or remote monitoring station 104 or registered as an alarm on the viewing device 118.

Each wireless tracking device 102 includes a circuit board 140 having an autonomous power supply, a microcontroller 138 and communication means 112 positioned thereon, interconnected by an electrical network by conventional electrical elements as is well known and used in the arts. Conventional wires connect the circuit board 140 with the microcontroller 138, activation button 126, and the alarm button 128. The circuit board 140 may be formed of silicon, fiberglass, KAPTON®, MYLAR, or other suitable materials that remain stable in a wide range of extreme temperatures that are well known and used in the arts. An antenna 142 is electrically connected to the microcontroller 138 on the circuit board 140 or alternatively imbedded within the microcontroller 138.

Microcontroller 138 may be any type of computer processor, such as, but not limited to, a central processing unit (CPU), a microprocessor, a video processor, a front end processor, a coprocessor, a single-core processor, a multi-core processor, and the like.

Microcontroller 138 is positioned within the wireless tracking device 102 and includes computer executable instructions 144, where the computer executable instructions 144 are operative to perform all the necessary functions for the system 100 and methods disclosed herein. Computer executable instructions 144 may be loaded directly on the wireless tracking device's microcontroller 138, or may be stored in the wireless tracking device's storage means, such as, but not limited to, computer readable media, such as, but not limited to, a hard drive, a solid state drive, a flash memory, random access memory, CD-ROM, CD-R, CD-RW, DVD-ROM, DVD-R, DVD-RW, and the like. The computer executable instructions 144 may be any type of computer executable instructions 144, which may be in the form of a computer program, the program being composed in any suitable programming language or source code, such as C++, C, JAVA, JavaScript, HTML, XML, and other programming languages.

Computer executable instructions 124 are operative to perform any all the necessary functions for the system 100 and methods disclosed herein which may include any one or more of the following: determine and store absolute location information 110 of each wireless tracking device 102 provided to group members, determine, gather and store location information 110 for generating reports.

Viewing device 118 may be any type of mobile communicating device configured with means for communicating wirelessly and/or wired, such as but not limited to, cellular phones (e.g., an iPhone, Android, Palm, Blackberry, or any "smart phone" as are generally known and used in the arts), location-aware portable phones (such as GPS), a personal computer, server computer, or laptop or netbook computer, a personal digital assistant ("PDA") such as a Palm-based device or Windows CE device, a laptop computer, a tablet personal computer, a portable screen, a portable processing device and/or any other portable device capable of communicating wirelessly over a computer network, local area network, wide area network such as the Internet, or any other type of network device that may communicate over a network.

Determining means 114 as referenced herein includes e.g. a GPS transponder, which upon activation, orients itself and determines the individual's location information 110. Determining means 114 also searches for signals of GPS satellite constellation 115, verifying whether wireless tracking device 102 has direct access to a satellite network system 115.

Viewing device 118 may include various hardware components, e.g. displaying means 146, such as, but not limited to: a liquid crystal display ("LCD") screen, a light emitting diode ("LED") display, touchpad or touch screen display, and/or any other means known in the arts for emitting a visually perceptible output. Viewing device 118 also includes a microcontroller 138 that is in electronic communication with one or more antennas 142, 142', a battery and its displaying means 146. In other embodiments, displaying means 146 is wirelessly connected to the microcontroller 138. Displaying means 146 may include a control means, such as, but not limited to, a touch screen, a stylus, and the like. In some embodiments, displaying means 146 may be electronically connected according to the hardware and software protocols that are known and used in the arts. In some embodiments, viewing device 118 also includes an alarm button 128' and an activation button 126'.

Viewing device's microcontroller 138' controls its displaying means 146, which is configured for displaying the identification information 120 for each individual provided with a wireless tracking device 102 within the group. Identification information 120 includes but is not limited to the individual's absolute geographical location, i.e. latitude, longitude, altitude, speed, battery life (for the wireless tracking device 102), date, time, location information 110 relative to other group members; or location information 110 relative to the group leader and or a secondary group leader in the event the group leader is unable to receive or respond appropriately to the received location information 110.

Viewing device 118 also includes computer executable instructions 144 configured for launching a user interface application 148 for generating reports. Exemplary reports may include but is not limited to idle reports (reporting idle time for stationary wireless tracking devices 102, 102'), geo-fence reports (reporting individual wireless tracking device that may have or almost strayed beyond the geo-fence perimeter 108), panic reports and the like.

FIGS. 2A-2D, show illustrative views of a system 100 of tracking individuals according to an embodiment of the present invention and the rotating map display 122 oriented in accordance with the geographical location of the group leader's or secondary group leader's wireless tracking device 102".

Figure 3:
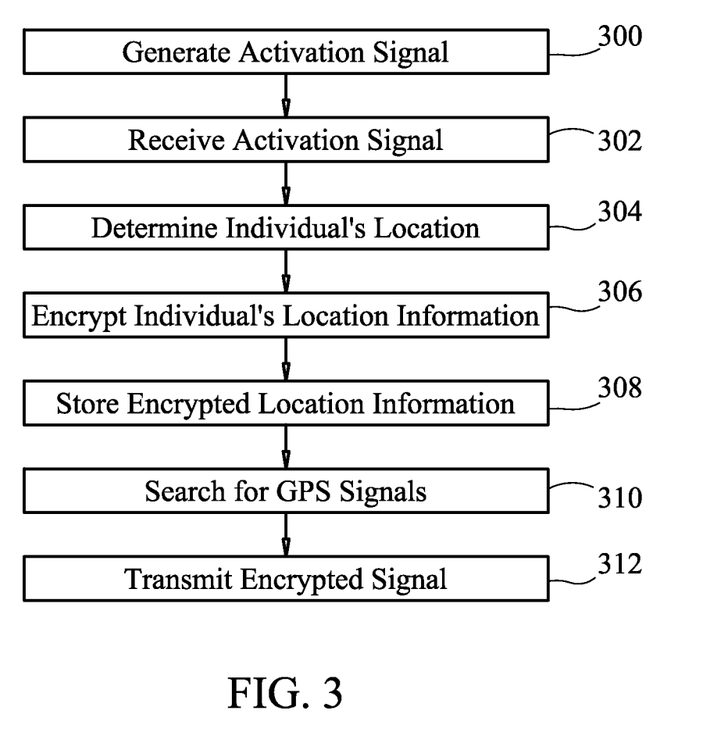
FIG. 3 is an exemplary method according to an embodiment of the invention.

FIG. 3 is an exemplary method 300 according to an embodiment of the invention. Upon activation, microcontroller 138 of wireless tracking device 102 causes an activation signal to be generated (step 302). Communication means 112 receives the activation signal in step 302. Communication means 112 is configured to receive at least one encrypted alarm signal 116 from a monitoring center 104 and/or an encrypted signal 116 containing an individual's location information 110 from a neighboring wireless tracking device 102 within the tracked group.

Each wireless tracking device's microcontroller 138 includes determining means 114 e.g. a GPS transponder 202 (not shown), which upon activation, orients itself and determines the individual's location information 110 (step 304). Microcontroller 138 creates an encrypted signal 116 (step 306) containing the individual's location information 110, which is stored in the wireless tracking device's 102 memory means 211 (step 308). Memory means 211 may include one of, or a combination of, but is not limited to RAM, SRAM, DRAM storage media or any other form of recording and storage media that are well known and used in the arts suitable for practicing the invention.

Determining means 114 searches for signals of GPS satellite constellation 115 (step 310), verifying whether wireless tracking device 102 has direct access to a satellite network system 115. If so, communication means 112 transmits the encrypted signal 116 (step 312) directly to the satellite network system 115, which re-transmits the encrypted signal 116 to the monitoring center 104. In one embodiment of the present invention, communication means 112 may communicate with monitoring center 104 via either a geosynchronous (GEO) or Low Earth Orbit (LEO) satellite in a network.

Figure 4:
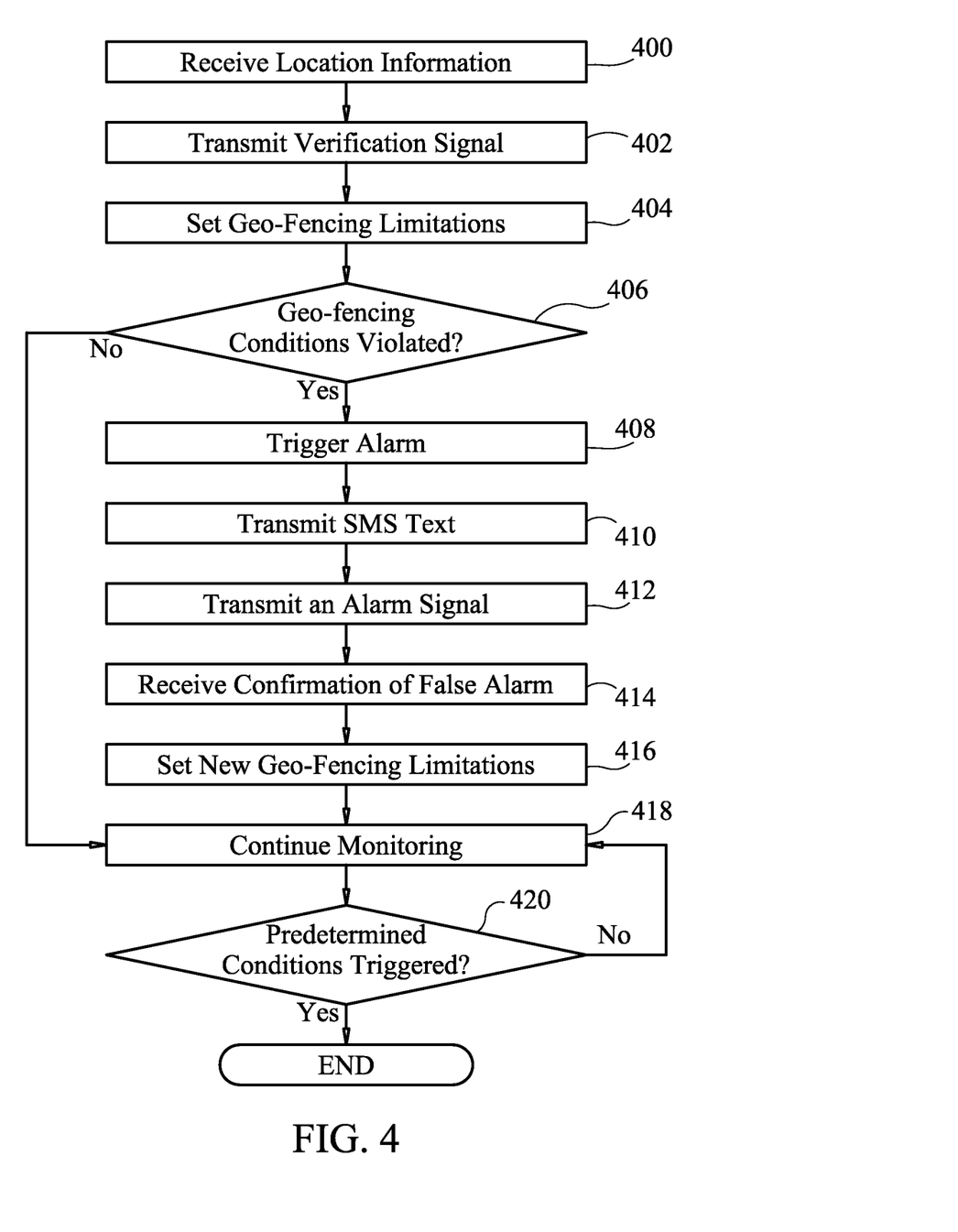
FIG. 4 shows a map for which the geo-fence limitations have been set according to an embodiment of the present invention.

Referring to FIG. 4, tracking may occur at a stationary, brick and mortar site or wirelessly via a wireless tracking device 102. Communications between the individuals being tracked and monitoring center 104 and/or wireless tracking device 102 (collectively "monitoring center 104") are bi-directional, wherein monitoring center 104 may also communicate with, for example, a designated group leader and/or other individuals within the tracked group. When wireless tracking device 102 is activated, monitoring center 104 receives the location information 110 (step 400) from each activated wireless tracking device 102 and verifies each individual's location information 110 by transmitting a verification signal (step 402) to each wireless tracking device 102 via either a GSM communications network, or to a satellite network system 115, which transmits the signal 116 to the individual wireless tracking devices 102, 102', 102". Each wireless tracking device 102 acts as nodes and/or routers wherein radio communications flow from one wireless tracking device 102 to another. In this manner, the range of radio communications is only limited to the distance between any two of the nearby wireless tracking devices 102, 102', 102r, allowing the group as a whole to be dispersed over a radius of several miles.

Monitoring center 104 sets geo-fencing limitations for the group's individuals (step 404) in real-time based on the group's center of gravity as they travel. Monitoring center 104 confirms whether geo-fencing conditions have been violated (step 406) by any individuals within the group by determining each individual's location relative to the pre-defined geo-fencing limitations, i.e. relative distance between individual members of the group, to confirm that individuals are still within predefined geo-fencing limitations. If during a tracking session, which is recorded by the viewing device 118, no geo-fencing conditions have been violated, monitoring center 104 will continue to monitor the individuals (step 418), until the tracking session terminates by virtue of a predetermined condition (step 420), e.g. notification of group arriving at their target destination, pre-defined time has elapsed in combination with no alarm conditions being reported or determined, and/or any other suitable predetermined conditions for terminating the tracking session without compromising the safety of the tracked group.

If the monitoring center 104 in step 406 determines that an individual has strayed beyond the pre-defined geo-fencing limitations for the group, an alarm will be triggered (step 408) at monitoring center 104, wherein the monitoring personnel may require continuation with the group leader, that the individual's location is known or that it is a false alarm. Accordingly, monitoring center 104 or the wireless tracking device 102 may transmit a message (step 410) via SMS text through a GSM communications network and/or an encrypted alarm signal 116 (step 412) over the satellite network system 115 notifying the group leader of the potentially alarming condition, i.e. missing individual.

The wireless tracking device's 102 communication means 112 receives the SMS text, e.g. ("JOHN IS 50 YARDS AWAY AND MAY BE MISSING, CONFIRM IF THIS IS A FALSE ALARM') and/or encrypted signal 116 where microcontroller's decrypting means 152 (not shown) decrypts the signal 116 for display in text and/or visual format on a group leader's wireless viewing device 118. Each wireless tracking device 102, 102', 102" acts as nodes and/or routers where their communications means 114 facilitate the group leader's wireless navigational unit 210 receipt of the transmitted SMS text. The wireless navigational unit 210 may comprise of a cell phone, portable display unit or other like communications devices e.g. PDA, Blackberry®, that are well known and used in the art for receiving and/or displaying wireless communications.

Upon receipt of the encrypted alarm signal, wireless tracking device's microcontroller 138 activates the alarm notification means 154 (not shown), causing for example, the sounding of an audio alarm or flashing a light, thereby alerting the group leader of the received encrypted alarm signal 116. In this manner, if the group leader lacks wireless access to a GSM network system and is unable to receive the SMS text, the group leader is visually and/or audibly alerted of the potential alarm and can take the necessary remedial steps to confirm the whereabouts of, and secure the group's individuals.

When the group leader receives the alarm, monitoring center 104 may require group leader to transmit a signal 116 and/or message confirming that it's a false alarm as the individual's location was known and/or authorized. As such, monitoring center 104 may receive confirmation (step 414) of false alarm and may also set new geo-fencing limitations (step 416) to incorporate the individual's authorized presence away from the group's center of gravity. Thereafter, monitoring center 104 may continue tracking (step 418) the group until the predetermined condition is triggered (step 420) at which time the tracking session terminates.

Figure 5:
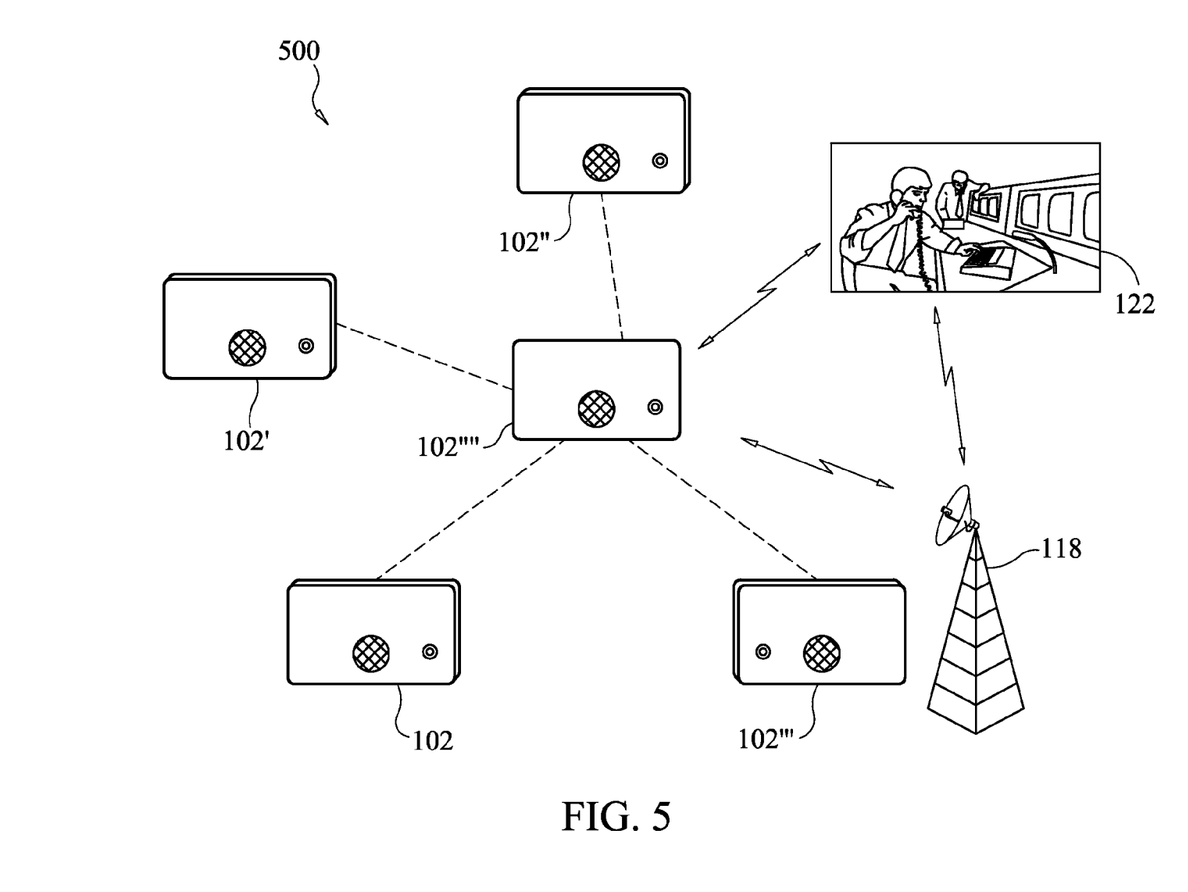
FIG. 5 illustrates a system of tracking a plurality of wireless tracking devices in accordance with an embodiment of the invention.
Figure 6:
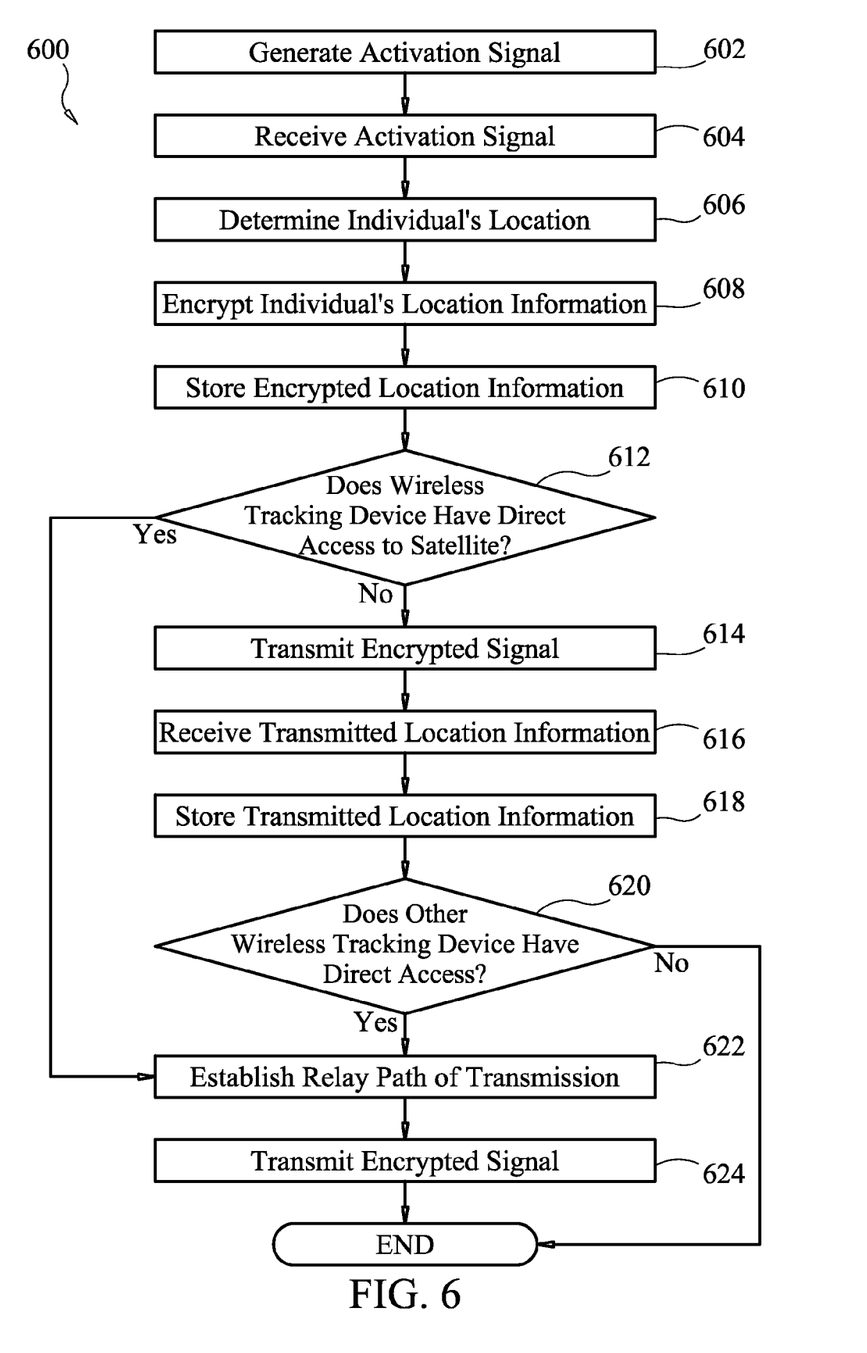
FIG. 6 is an illustrative view of a particular individual being tracked wherein the map rotated according to the location and/or heading information for the individual according to an embodiment of the present invention.

Referring to FIGS. 5 & 6, a system 100 and method 600 of tracking a plurality of wireless tracking devices 102, 102', 102"', 102" in accordance with an embodiment of the invention and an illustrative view of a method 600 of an exemplary embodiment of the present invention are shown. A group leader's wireless tracking device 102 may be configured to activate at least one or more, and/or all of the wireless tracking devices 102', 102'', 102''', 102'' for the individuals within his/her group. Upon activation, the group leader's wireless tracking device's 102 microcontroller 138 causes an activation signal to be generated (step 602) and each wireless tracking device 106, 108, 110, 111, 112 receives the activation signal (step 604), determine individual's location via the individual's wireless tracking device 102 (step 606); encrypt individual's location information 110 (step 608).

Additionally, microcontroller's 136 determining means 114 searches for signals of GPS satellite constellation to verify whether wireless tracking device 102 has direct access to a satellite network system 115 (step 610). If wireless tracking device 102 has direct access, microcontroller 138 establishes a relay path of transmission in step 620 and transmits the encrypted signal (step 622) containing the individual's location information directly to the wireless communications network system 115 (not shown), which re-transmits the encrypted signal to either monitoring center 104 and/or the wireless tracking device 102.

However, not all wireless tracking devices 102, 102' 102'', 102''' within the group may have direct access to a satellite network system 115. As such, a wireless tracking device 102 may randomly query one or more neighboring wireless tracking devices 102, 102' in a manner similar to mesh network systems, to determine whether a wireless tracking device 102 has direct access to a satellite network system 115. It is understood that this mesh network is dynamically formed on an ad-hoc basis as a wireless tracking device 102 systematically queries other neighboring wireless tracking devices 102, 102' 102'', 102''' for the most direct route to the satellite network system 115 until a wireless tracking device 112 with direct access to a satellite network system 115 is located.

If microcontroller 138 determines that the wireless tracking device 102 does not have direct access to a satellite network system 115, the encrypted signal containing individual's location information is transmitted (step 612) to each neighboring wireless tracking device 106, 102, 102' 102'', 102''' that is queried for direct access, where wireless tracking device's location information 110 is received (step 614) and stored thereon (step 616). However, the first neighboring wireless tracking device 102 queried may also lack direct access. Microcontroller 138 will therefore query other wireless tracking devices 108, 110, 112 to determine if any other wireless tracking devices 102, 102', 102'' have direct access (step 618). If direct access cannot be found, microcontroller 138 will cease its query and retain the location information 110 for future transmission.

As microcontroller 138 queries neighboring wireless tracking devices, it is also dynamically establishing a relay path of transmission (step 620) for the most efficient path of transmission of the individual's location information to monitoring center 104. Therefore, if the first neighboring wireless tracking device queried lacks direct access, a second and then a third, etc. will be queried for direct access in step 622.

Once the relay path of transmission has been established and a wireless tracking device 102 with direct access to a satellite network system 115 is found, communication means 112 of that wireless tracking device 102 will thereby transmit an encrypted signal as in step 622 containing the location information 110 for each wireless tracking device 102, 102' 102'', 102''' that was transmitted and received. Each wireless tracking device 102, 102' 102'', 102''' within the group that lacked direct access to the satellite network system 115 will similarly transmit its location information 110 for each individual along the same dynamically created relay path for transmission to monitoring center 104 via the wireless communications network systems 116.

Wireless tracking device 102 communicates with the communications network systems 116 via its short range protocol or wireless local area network (WLAN). In this manner, each individual's location information is transmitted and stored with a neighboring wireless tracking device 102 for later transmission as needed. Thus, the location information being transmitted to the monitoring center 104 may therefore include anyone or more of the following: the absolute geographical location for one, or a plurality of individuals wearing the wireless tracking device in the tracked group. Monitoring center 104 is thus able to monitor signals received from each wireless tracking device 102, 102' 102'', 102''' and able to locate the group and/or its individuals at any given point in time during a tracking session.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the system 100 and method 101 describe above and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:
1. A system for tracking a group of individuals comprising:
   a wireless tracking device provided to a group leader and at least one or more members within a tracked group, wherein each wireless tracking device is enabled for bi-directional communications with a monitoring center, and is enabled to determine and store absolute location information of the group member's wireless tracking device relative to the group leader's wireless tracking device's location, and store at least one other neighboring group member's wireless tracking device's location information;
   a geo-fence, having a dynamic perimeter, the geo-fence being around the one or more group members, and the elements of the geo-fence being established by the monitoring center in real-time for all group members provided with the wireless tracking device based on the group's center of gravity as they travel, whereby the geo-fence is in constant motion and is determined by first determining where a majority of the group members are located and calculating a maximum allowed distance between the group leader and the majority of the group members;
   communication means enabled for transmitting to or from the monitoring center via a satellite network system, an encrypted signal containing the group member's wireless tracking device's location information and/or the neighboring group member's wireless tracking device's location information, along a dynamically created relay path of transmission; and viewing devices enabled for displaying the group member's wireless tracking device's location information relative to any one of the group leader's location and a secondary group leader's location on a rotating map display, wherein the rotating map display is displayed as oriented and rotated relative to any one of the group leader's geographical location and the secondary group leader's geographical location.

2. The system of claim 1, wherein the wireless tracking device includes an alarm button for notifying the group leader or the monitoring center of needed assistance.

3. The system of claim 1, wherein the identification information includes any one or more of the following: name, absolute location, rank, blood type, or unique identifier.

4. The system of claim 1, wherein the wireless tracking device's communication means communicates any one or more of the following in real-time: latitude, longitude, altitude, speed, battery life, date, time, location information relative to other group members; or location information relative to group leader.

5. The system of claim 1, wherein the viewing device is enabled for displaying location information for each group member's wireless tracking device relative to any one other group member.

6. The system of claim 1, wherein the viewing device is configured to record and store at least one tracking session of all wireless tracking devices within the group as tracked and captured in a rotational map display for the duration of the tracking session.

7. The system of claim 6, wherein the viewing device is configured to replay the at least one tracking session.

8. The system of claim 1, wherein the viewing device is configured with a user interface, which includes computer executable instructions for generating reports.

9. The system of claim 1, wherein said location information being transmitted to monitoring center may include anyone or more of the following: the absolute geographical location for one, some or all individuals wearing the wireless tracking device in the group.

10. The system of claim 1, wherein viewing devices are enabled for displaying identification information concerning the group member's wireless tracking device on a rotating map display.

11. A method for tracking a group of individuals comprising the steps of:

providing a wireless tracking device to a group leader and at least one or more members within a tracked group, wherein each wireless tracking device is enabled for bi-directional communications with a monitoring center;

establishing dynamic geo-fencing elements in real-time for all group members provided with wireless tracking devices based on the group's center of gravity as they travel, whereby the geo-fence is in constant motion and has a dynamic perimeter, and each wireless tracking device is enabled to determine and store absolute location information of the group member's wireless tracking device relative to the group leader's wireless tracking device's location and store at least one other group member's wireless tracking device's location information;

determining the boundaries of the geo-fence by first determining where a majority of the group members are located and calculating a maximum allowed distance between the group leader and the majority of the group members;

transmitting to or from the monitoring center by communication means via a satellite network system, an encrypted signal containing the group member's wireless tracking device's location information and/or a neighboring wireless tracking device's location information, along a dynamically created relay path of transmission; and displaying on viewing devices provided to the group members, the group member's wireless tracking device's location information relative to any one of the group leader's location and a secondary group leader's location on a rotating map display, wherein the rotating map display is displayed as oriented and rotated relative to any one of the group leader's geographical location and the secondary group leader's geographical location.

12. The method of claim 11, wherein the wireless tracking device includes an alarm button for notifying the group leader or the monitoring center of needed assistance.

13. The method of claim 11, wherein the identification information includes any one or more of the following: name, absolute location, rank, blood type, or unique identifier.

14. The method of claim 11, wherein the wireless tracking device's communication means communicates any one or more of the following in real-time: latitude, longitude, altitude, speed, battery life, date, time, location information relative to other group members; or location information relative to group leader.

15. The method of claim 11, further comprising displaying location information for each group member's wireless tracking device relative to any one other group member.

16. The method of claim 11, wherein the viewing device is configured to record and store at least one tracking session of all wireless tracking devices within the group as tracked and captured in a rotational map display for the duration of the tracking session.

17. The method of claim 16, wherein the viewing device is configured to replay the at least one tracking session.

18. The method of claim 11, wherein the viewing device is configured with a user interface, which includes computer executable instructions for generating reports.

19. The method of claim 11, wherein said location information being transmitted to monitoring center may include anyone or more of the following: the absolute geographical location for one, some or all individuals wearing the wireless tracking device in the group.

20. The method of claim 11, further comprising displaying on the viewing device identification information concerning the group member's wireless tracking device on a rotating map display.

* * * * *